United States Patent [19]
Bonfield et al.

[11] Patent Number: 5,728,753
[45] Date of Patent: Mar. 17, 1998

[54] BIOACTIVE COMPOSITE MATERIAL FOR REPAIR OF HARD AND SOFT TISSUES

[75] Inventors: William Bonfield, Welwyn; Min Wang, London, both of England; Larry L. Hench, Gainesville, Fla.

[73] Assignees: University of London, London, England; University of Florida, Gainesville, Fla.

[21] Appl. No.: 556,016

[22] Filed: Nov. 9, 1995

[51] Int. Cl.⁶ .................. C08K 3/32; C08L 23/00
[52] U.S. Cl. .......... 523/114; 523/113; 523/115; 524/414; 524/494; 524/583; 524/586; 524/791; 424/422; 623/13
[58] Field of Search .................. 524/791, 494, 524/586, 414, 583; 523/113, 114, 115; 424/422; 623/13

[56] References Cited

U.S. PATENT DOCUMENTS

| | | | |
|---|---|---|---|
| 5,017,627 | 5/1991 | Bonfield et al. | 523/115 |
| 5,068,122 | 11/1991 | Kokubo et al. | 427/2 |
| 5,263,992 | 11/1993 | Guire | 623/66 |

FOREIGN PATENT DOCUMENTS

| | | | |
|---|---|---|---|
| 9059870 | 6/1974 | Japan | 524/586 |

*Primary Examiner*—Andrew E. C. Merriam
*Attorney, Agent, or Firm*—Burns, Doane, Swecker & Mathis, LLP

[57] ABSTRACT

Composites suitable for use as prostheses for attachment to soft tissues, such as cartilage, tendons, skin, tympanic membrane and gingiva, as well as to cancellous or trabecular bone, are based on combination of a polyolefinic binder with certain bioactive glass materials. The composites bond actively with soft tissues and are readily formulated achieve mechanical properties comparable to those of the soft tissue of interest.

10 Claims, 7 Drawing Sheets

BIOACTIVE COMPOSITE MATERIAL FOR REPAIR OF HARD AND SOFT TISSUES

BACKGROUND OF THE INVENTION

1. Field of the Invention

The present invention relates to composite materials, and in particular to materials suitable for surgical implantation as replacements for various hard and soft tissue structures.

2. Description of the Related Art

Historically, materials used in endoprosthesis (i.e., the replacement of internal anatomical structures with artificial appliances) have largely been "bioinert". Metallic alloys, such as stainless steel or cobalt chromium, are typically superior in strength to the structures they replace but do not interact chemically or interfacially with surrounding tissue. Although they avoid the many problems arising from tissue incompatibility, bioinert materials can never become fully integrated within their in vivo environment. As a consequence, the prosthesis frequently detaches from the tissue to which it was originally affixed, resulting in prosthetic loosening. Moreover, modulus mismatching between the appliance and the replaced structure can lead to stress shielding, resulting in poor mechanical compatibility. Bioinert ceramics such as alumina, for example, are stiffer than bone and also exhibit inferior fracture toughness.

An alternative approach is disclosed in U.S. Pat. No. 5,017,627, which sets forth various compositions that, when fabricated and implanted as prosthetic devices, remain anchored to surrounding tissue. The composite materials described in the '627 patent are based on a polyolefinic binder containing a particulate inorganic solid. Disclosed particulate solids include calcium salts such as hydroxyapatite (HA) or fluorapatite, chalk, flyash and silica. Instead of remaining biologically inert, the composite materials instead exhibit "bioactive" behavior, establishing interfacial bonds to compact bone. The ratio of polyolefin to particulate material can be varied to obtain different values of Young's modulus and strain-to-failure and different amounts of interfacial bonding. Importantly, the composite can be made ductile.

While versatile, this type of material exhibits certain limitations. In particular, the range of mechanical properties obtainable according to the '627 patent is relatively limited due to the high HA loading levels necessary to achieve bioactivity. The available values of Young's modulus, for example, tend to be comparable with compact (cortical) bone, but not cancellous bone or soft tissues.

Moreover, soft tissues (such as tendons, ligaments, cartilage and skin) tend to be among the most resistant to adhesion altogether. Even composites containing very high HA concentrations do not stimulate significant interfacial bonding in such tissues. Thus, current materials are both mechanically and chemically unsuited as prostheses for repair of soft-tissue structures.

DESCRIPTION OF THE INVENTION

Objects of the Invention

Accordingly, it is an object of the present invention to provide composite materials that exhibit high degrees of bioactivity and rapidly establish interfacial bonds with surrounding tissue.

It is another object of the invention to achieve, with synthetic bioactive materials, mechanical compatibility with a range of hard and soft tissues.

It is still another object of the invention to provide prosthetic replacements whose bioactivity level can be selected to achieve a wide range of predetermined, in vivo attachment durations.

Other objects will, in part, be obvious and will, in part, appear hereinafter. The invention accordingly comprises an article of manufacture possessing the features and properties exemplified in the constructions described herein and the several steps and the relation of one or more of such steps with respect to the others and the apparatus embodying the features of construction, combination of elements and the arrangement of parts that are adapted to effect such steps, all as exemplified in the following summary and detailed description, and the scope of the invention will be indicated in the claims.

Brief Summary of the Invention

We have found, quite surprisingly, that a polyolefinic binder can be combined with certain bioactive glass materials to produce composites that not only retain high bioactivity levels, but may also be formulated to achieve mechanical properties comparable to various soft and hard tissues over a variety of parameters, including tensile strength, fracture strain, and Young's modulus.

Bioactive glasses are well-known compositions that elicit specific physiological responses, including the provision of surface-reactive silica, calcium and phosphate groups and alkaline pH levels at interfaces with tissues. In particular, glasses composed of $SiO_2$, $Na_2O$, $CaO$ and $P_2O_5$ exhibit substantial bioactivity, with compositions having $SiO_2$ levels ranging from 42% to 52% bonding to bone much more rapidly than HA. See, e.g., Hench, "Bioceramics: From Concept to Clinic," 74 *J. Amer. Ceram. Soc.* 1487 (1991). Such compositions also bond with exceptional efficacy to soft connective tissues.

These advantageous characteristics arise as a result of chemical reactions occurring at the surface of the glass when exposed to ambient body fluids. Ion exchange and irregular surface dissolution forms a hydrated silica gel layer that increases the presented area and enhances formation of a microcrystalline biological apatite layer on the roughened glass. This layer, which can form in as little as a few hours in vivo, bonds not only to bone but also to collagen fibrils. The latter type of bonding, which cannot be achieved by materials such as HA or polymeric compositions (or, obviously, by bioinert materials), is required for soft-tissue bonding. Furthermore, bioactive glass in bulk form bonds to bone with significantly greater rapidity and completeness than does HA.

By retaining the interfacial and chemical properties of bioactive glasses, the composites of the present invention offer unique advantages as soft-tissue prostheses and for prostheses that bond to cancellous or trabecular bone or cartilage. Our composites can be compression or injection molded into appliances for replacement of or bonding to a variety of soft tissues. As used herein, the term "soft tissue" is intended to embrace cartilage, tendons, ligaments, skin, tympanic membrane, gingiva, subcutaneous tissue, and all collagen-based connective tissue.

BRIEF DESCRIPTION OF THE DRAWINGS

The foregoing discussion will be understood more readily from the following detailed description of the invention, when taken in conjunction with the accompanying drawings, in which.

DETAILED DESCRIPTION OF THE PREFERRED EMBODIMENTS

Figure 1:
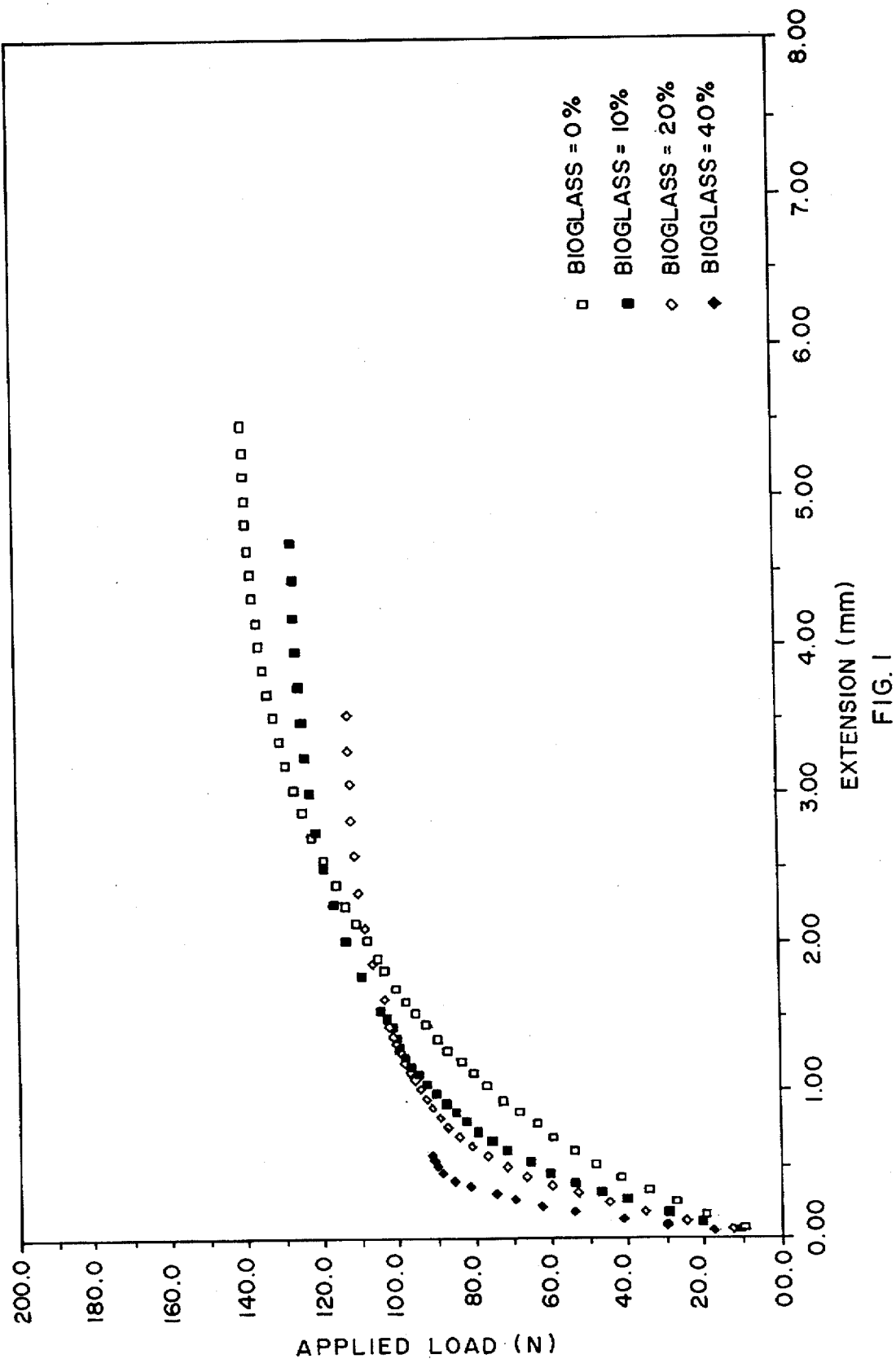
FIG. 1 graphically compares ductility for composites having bioactive-glass volume loading fractions of 0%, 10%, 20%, and 40%.

The preferred embodiment of the present invention is a composite material comprising a particulate bioactive glass dispersed in a solid-phase polyolefin binder. The bioactive glass formula should contain 42–52% $SiO_2$, and a suitable material is the 45S5 BIOGLASS® product (45 wt% $SiO_2$, 6 wt% $P_2O_5$, 24.5 wt% CaO, 24.5 wt% $Na_2O$) marketed by U.S. Biomaterials Corp., Baltimore, Md. 21236. However, other bioactive glass formulations with up to 52 wt% $SiO_2$ can be used instead.

The polyolefin binder is preferably a homo- or copolyolefin having a weight-average molecular weight, $<M_w>$, greater than 20,000, suitably greater than 100,000, and preferably in excess of 300,000, and suitably below 3,000,000 but preferably below 1,000,000. Binders with $<M_w>$ below 20,000 may not exhibit sufficient biocompatibility, while those with $<M_w>$ above 3,000,000 present processing difficulties. High-density polyethylene (HDPE) in linear form is the preferred binder material, although advantageous results can also be obtained using linear or branched polypropylene, polybutylene, or a copolymer of ethylene and at least one of propylene, butylene and hexene.

As discussed in greater detail below, the glass loading fraction determines both the mechanical properties and bioactivity level of the resulting composite, and is therefore carefully chosen to achieve both tissue compatibility and a desired extent of attachment. Loading fractions in the range of 10% to 40% by volume are preferred; however, loading fractions of 5 to 50% by volume are acceptable. The bioactive glass is present in the form of ground particles. Size uniformity is not necessary to the present invention; particles having sizes ranging from 1.5 µm to 150 µm are preferred, sizes from 0.5 µm to 500 µm are acceptable.

1. Material Preparation

The composite materials of the present invention may be prepared first by compounding the polyolefin, preferably at a temperature above the softening point (in the case of HDPE, suitably between 200° to 260° C., and preferably between 200° and 240° C.) with the bioactive glass in dry, particulate form. The polyolefin is advantageously introduced into the compounder first, and the bioactive glass thereafter added in small quantities until the desired volume fraction is obtained. The compounding time depends on the identities and volume fractions of the binder and bioactive glass, but for a 0.5 kg charge a period of 1–2 hours is typical. Two-stage compounding may be utilized for relatively high particulate volume fractions. Alternatively, the composites may be blended by extrusion and re-extrusion, as well as by other suitable solid-phase mixing techniques.

The compounded composite is then molded by compression or injection to its final shape as a prosthesis, and at least a portion of its surface ground or machined to ensure adequate exposure of the glass particles. Different particle sizes or volume fractions of bioactive glass can be used during the molding or injection step to produce gradients in mechanical properties.

Using the compounding technique described above, we prepared composite materials from HDPE and 45S5 BIOGLASS® particles ranging in size from 1.5 µm to 150 µm, and with an average size of 45.7 µm, in particle/binder volume ratios of 10%, 20%, and 40%. Subsequent processing of the composites into specific compression-molded shapes preserved the dispersion of the bioactive glass phase, which was also undisturbed by machining, grinding, polishing or sand-blasting of the surfaces to expose the particles. For comparative purposes, we also prepared untilled (0% bioactive glass) HDPE samples in a similar manner. The following analyses were then performed on these materials.

2. Mechanical Properties

We prepared tensile test specimens from compression-molded composite plates 1.75 mm thick, with a gauge length of 25 mm, according to ISO Standard 527. We then conducted conventional tensile tests under ambient conditions with an Instron 6025 testing machine at a crosshead speed of 0.5 mm/min or 5.0 mm/min. The results appear in FIG. 1, and indicate that composites having bioactive-glass volume fractions of 30% or below exhibit considerable ductility.

Figure 2:
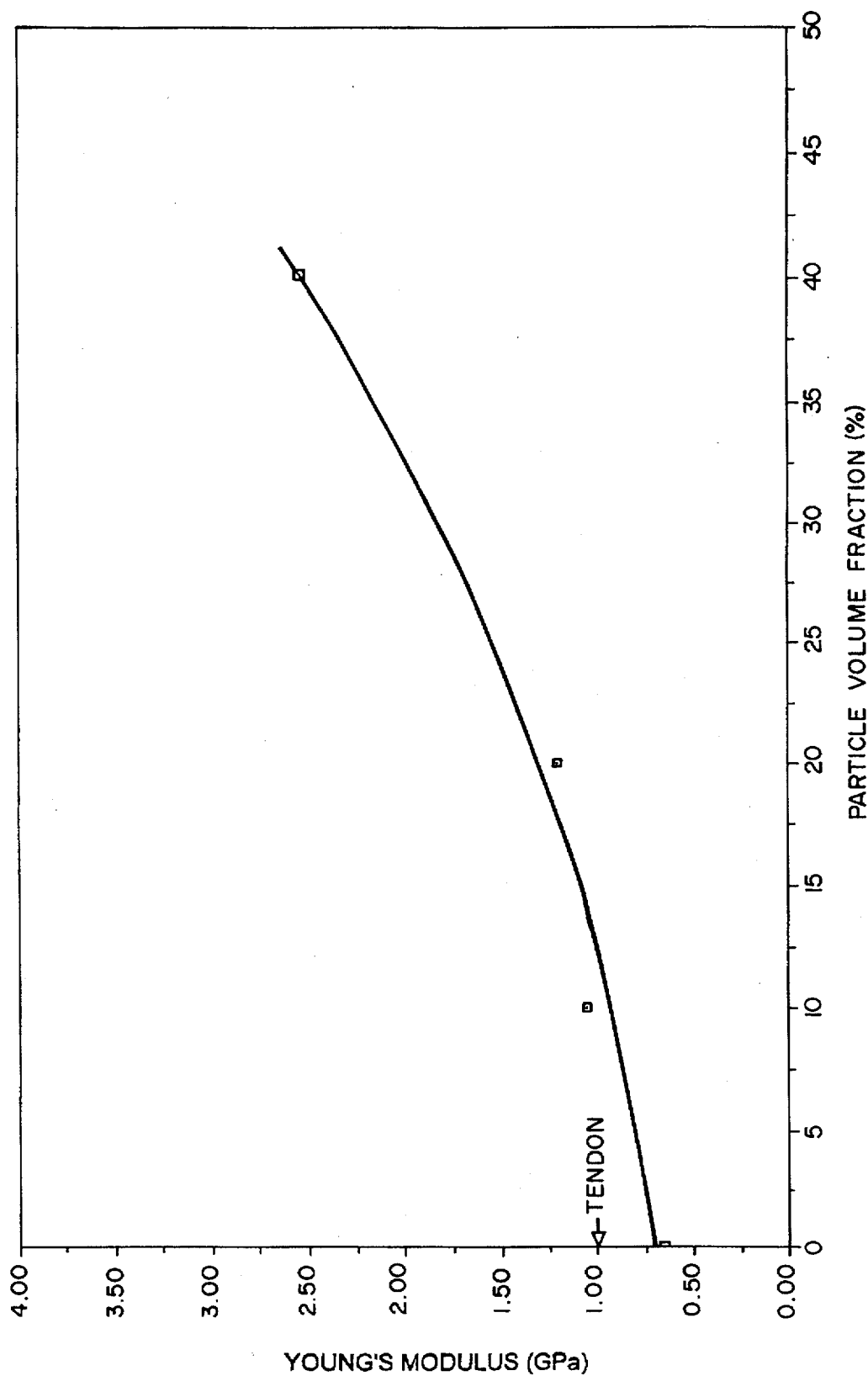
FIG. 2 graphically illustrates the dependence of Young's Modulus (GPa or giga pascal) on bioactive-glass volume loading fraction.
Figure 3:
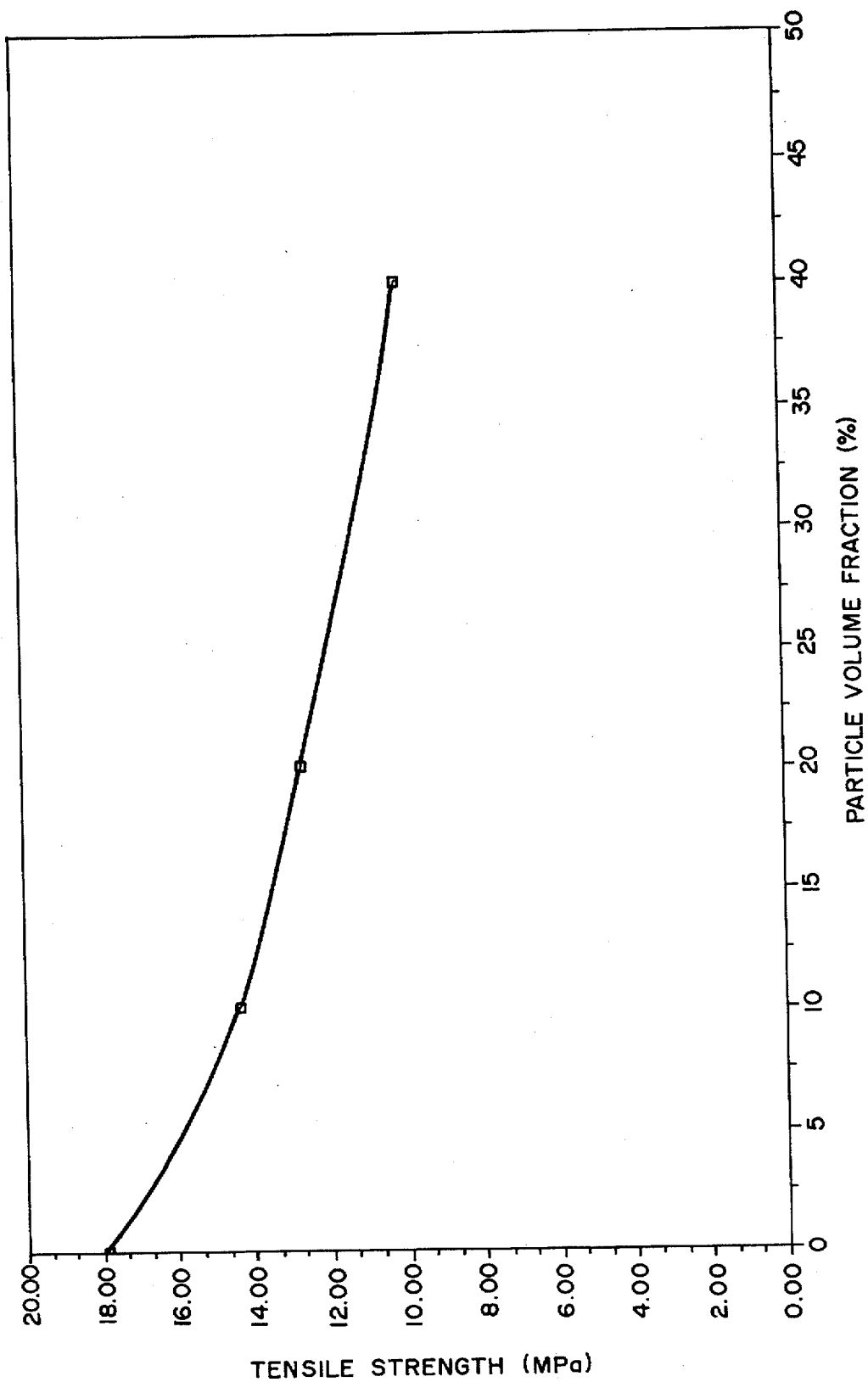
FIG. 3 graphically illustrates the dependence of tensile strength (MPa or mega pascal) on bioactive-glass volume loading fraction.
Figure 4:
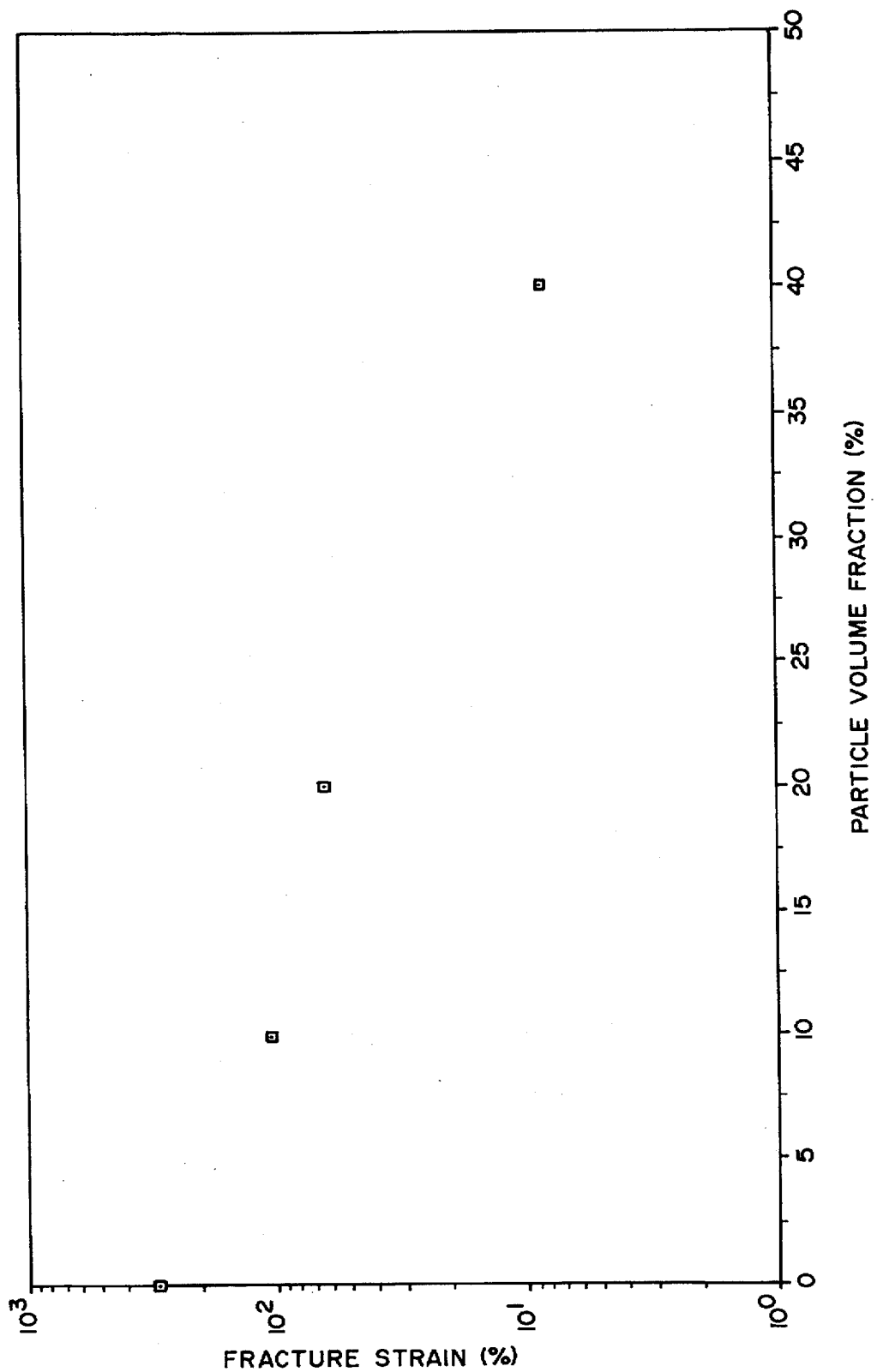
FIG. 4 graphically illustrates the dependence of fracture strain on bioactive-glass volume loading fraction.
Figure 5:
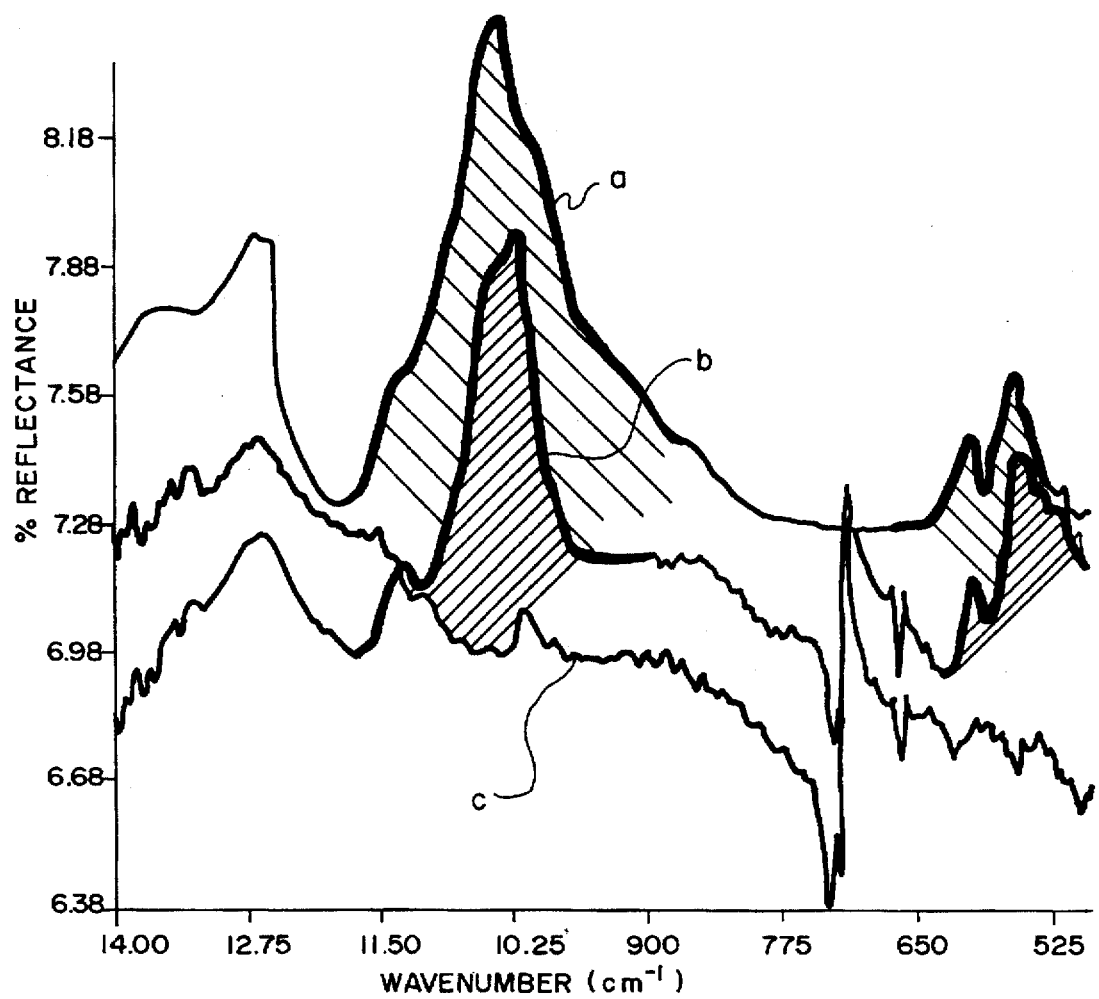
FIG. 5 is an inked rendition of a Fourier-transform infrared spectroscopy (FTIR) spectrum that illustrates the formation of biological apatite layers on various samples in a simulated body fluid containing no calcium or phosphate ions.

FIGS. 2–4 illustrate the effect of varying volume fractions on Young's modulus, tensile strength and fracture strain, respectively. As indicated in the following tables, composites with bioactive-glass volume fractions of 30% or below exhibit levels of elastic compliance, tensile strength and fracture strain comparable to those of soft connective tissues such as tendon, ligaments, articular cartilage, skin, tympanic membrane, and gingiva. Composites with bioactive-glass volume fractions in excess of 30% exhibit mechanical characteristics comparable to cancellous bone.

TABLE 1

| Particle | | Compression-Molded Material | | |
|---|---|---|---|---|
| Volume Fraction (%) | Particle Weight Percentage (%) | Young's Modulus (GPa) | Tensile Strength (MPa) | Fracture Strain (%) |
| 0 | 0 | 0.65 ± 0.02 | 17.89 ± 0.29 | >360 |
| 10 | 22.7 | 1.05 ± 0.04 | 14.34 ± 0.11 | 105.1 ± 56.6 |
| 20 | 39.8 | 1.21 ± 0.02 | 12.69 ± 0.07 | 64.0 ± 9.4 |
| 40 | 63.8 | 2.54 ± 0.16 | 10.15 ± 0.71 | 8.5 ± 2.8 |

TABLE 2

| Property | Cortical Bone | Cancellous Bone | Articular Cartilage | Tendon |
|---|---|---|---|---|
| Young's Modulus (GPa) | 7–30 | 0.5–0.05 | 0.001–0.01 | 1 |
| Tensile Strength (MPa) | 50–150 | 10–20 | 10–40 | 80–120 |
| Fracture Strain (%) | 1–3 | 5–7 | 15–50 | 10 |

3. Bioactivity

In a first experiment, we evaluated the bioactivity of composites having bioactive-glass volume fractions of 10%, 20%, and 40% by subjecting the samples at 37° C. to a simulated body fluid (SBF-tris) that does not contain calcium or phosphate ions. The rate of formation of a biological apatite layer on the surface, which can be measured using FTIR, is directly correlated with the level of bioactivity. FIG. 4 depicts three FTIR spectra obtained in the diffuse reflection mode for the 45S5 BIOGLASS® particles in isolation (a), the composite containing 40% bioactive glass particles (b), and the composite containing 10% bioactive glass particles (c) after reaction for 20 hours. The 20-hour time period is clinically significant, and is used for quality-assurance testing of bioactive glasses intended to bond with bone and soft connective tissue.

The shaded regions correspond to the molecular vibrational modes characteristic of a microcrystalline biological apatite layer. The spectra indicate that only the 40% composite and the pure bioactive glass particles developed the biological apatite layer in SBF-tris within 20 hours.

Figure 6:
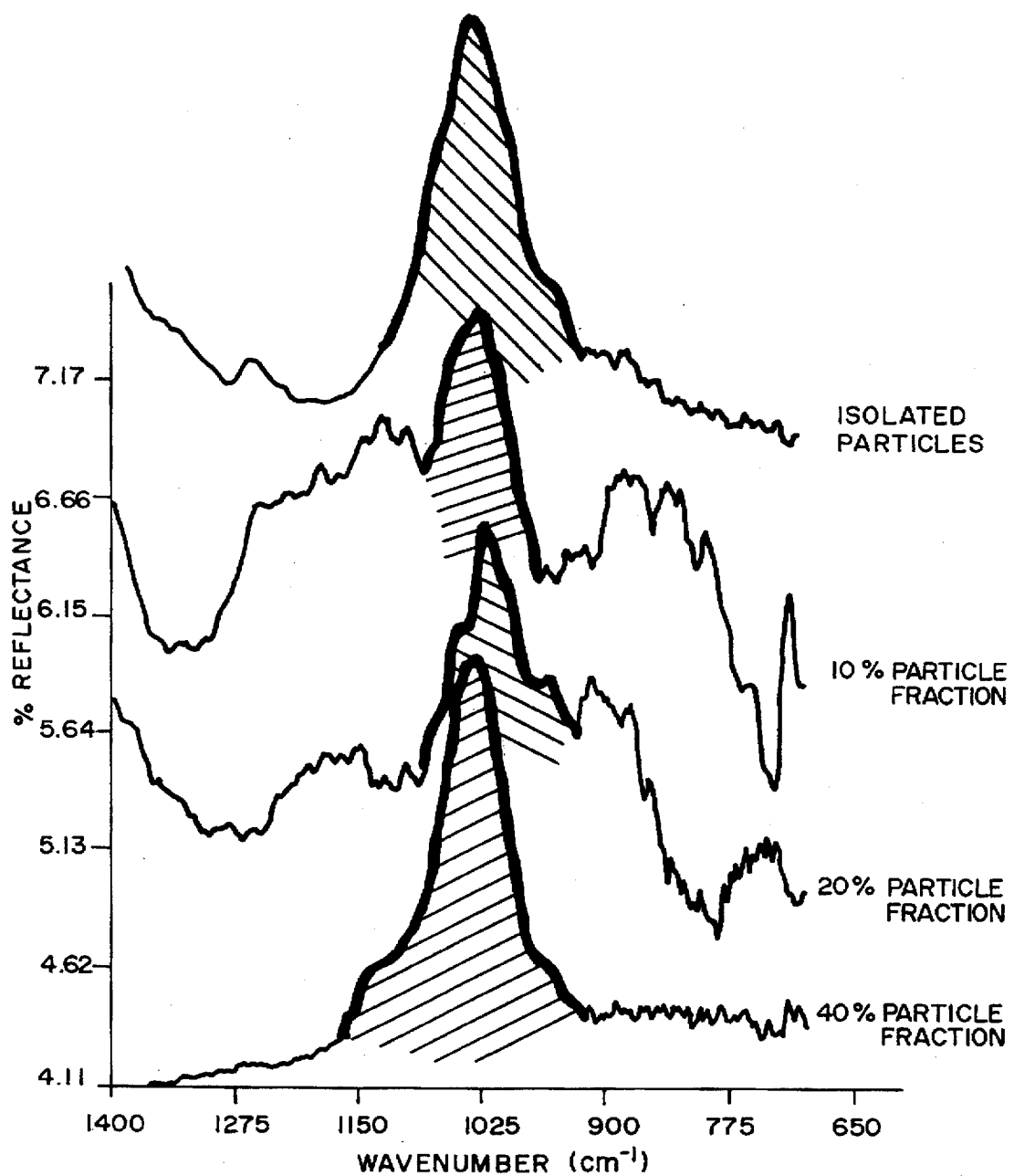
FIG. 6 is an inked rendition of an FTIR spectrum that illustrates the formation of biological apatite layers on various samples in a simulated body fluid that does contain calcium and phosphate ions.

In a second experiment, identical composites and the isolated particles were exposed for 20 hours at 37° C. to a simulated body fluid (SBF-9) that does contain calcium and phosphate ions. The resulting FTIR spectra, shown in FIG. 6, demonstrate that all of the composites develop surface biological apatite layers equivalent to that of the isolated glass particulate.

Figure 7:
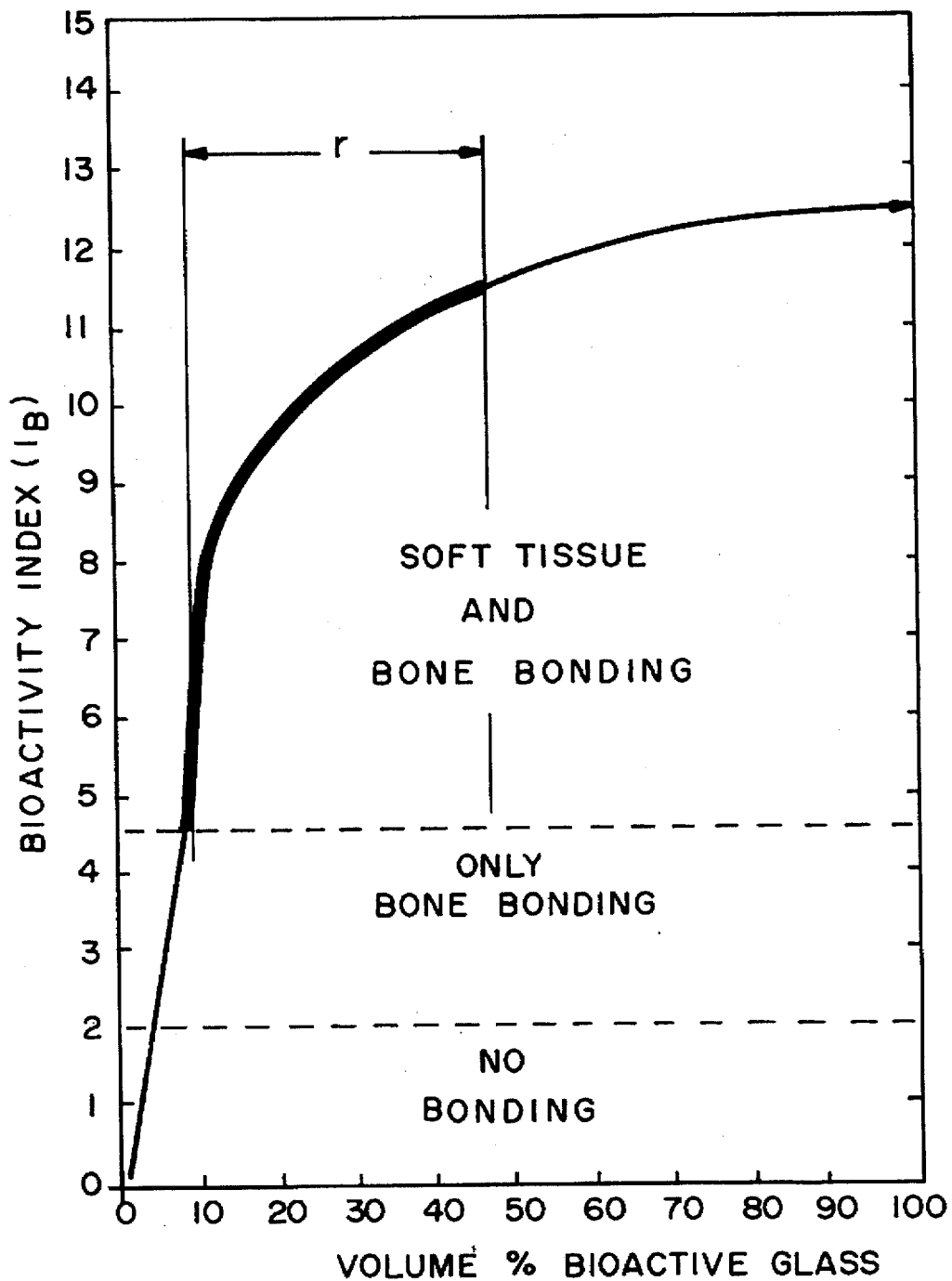
FIG. 7 illustrates the dependence of composite bioactivity on the bioactive-glass volume loading fraction.

The rate of apatite formation (i.e., the actual level of bioactivity), however, depends on the volume percentage of the bioactive glass phase. This is shown in FIG. 7, which graphically depicts the dependence of the composite's bioactivity on its bioactive-glass loading fraction. Bioactivity is expressed as the parameter $I_B$, defined as $100/t_{0.5bb}$, where $t_{0.5bb}$ is the time necessary for 50% of the composite surface to bond to tissue. The range r represents preferred bioactive-glass loading fractions.

4. Clinical Applications

In accordance with a further aspect of the invention, the composites are molded into prostheses for use in surgery. The ranges of bioactivity and mechanical properties of the composites facilitates the production of implants tailored for highly specific medical requirements. The invention is particularly well suited to implants requiring intimate contact with soft tissue (e.g., aeration tubes for the middle ear, which protrude through the tympanic membrane).

For example, present-day aeration tubes are frequently extruded within a year; because these devices must typically remain implanted for several years, patients often undergo multiple implantation surgeries to replace the failed tubes. The present invention not only provides tubes that will remain in place for the clinically indicated period, but also, through judicious selection of bioactivity level, allows the clinician to match this period with the degree of soft-tissue bonding most compatible therewith. Thus, as shown in FIG. 7, bioactive glass fractions of 10–20% by volume would be expected to exhibit little soft-tissue bonding, and therefore resemble most present-day aeration tubes; accordingly, composite formulations with this range of bioactive glass fraction are suitable for 1–2 years of use. By contrast, implants suitable for 2–4 years of use can be obtained using bioactive glass fractions in the range of 20–40%. The low elastic modulus of the composites of the present invention, particularly those having particulate volume fractions of 10–30%, discourages mechanical deterioration of the interface between the aeration tube and the tympanic membrane, while bioactivity provides adherence to the collagen fibrils of the membrane to hinder extrusion.

The low Young's modulus, high fracture strain and soft-tissue bonding characteristics associated with our composites (particularly those with particulate volume fractions of 10–30%) renders them uniquely well suited to use as percutaneous leads (e.g., to accommodate perfusion, in-dwelling catheters, electrodes for auditory or neuromuscular stimulation, etc.). The interfacial adhesion that results from soft-tissue bonding reduces the chance of infection, while high flexibility inhibits the formation of interfacial stresses, which can deteriorate the junction between the lead and surrounding tissue.

Repair of cartilage or cancellous bone or fixation of traditional orthopedic prostheses against such tissues can require establishment of an interface therebetween. Bioinert prostheses typically exhibit values of Young's modulus in excess of 100 GPa (giga pascal) and sometimes several orders of magnitude above the corresponding values for cancellous bone (see Table 2). Prostheses fabricated from the composites of the present invention offer values of Young's modulus far more compatible with those of cancellous bone and cartilage, while providing a bioactively derived tissue bond across the interface. Composites used in such prostheses may desirably be formulated with a gradient in the volume fraction of bioactive glass in order to achieve an optimal gradation in elastic properties, thereby maximizing fracture toughness without loss of interfacial bioactivity.

Prostheses may be fabricated from the composites of the present invention by compression or injection molding. In the former case, the solid composite is remelted, suitably, in the case of HDPE, at a temperature from 190° to 250° C., and preferably between 200° to 230° C.; then charged to the prosthesis mold cavity under load until the cavity is filled; and finally cooled under load. In the case of injection molding, similar temperatures are used, but care is taken to employ an injection pressure and speed low enough to avoid scorching.

It may prove desirable, especially with polyolefins having $<M_w>$ below 500,000, to gamma-irradiate the fabricated prosthesis, both for sterilization and to impart resistance to creep and environmental stress cracking. Where processing difficulties are encountered or expected, it is often desirable to employ a polyolefin of relatively low $<M_w>$, to facilitate convenient production of the composite, and then to irradiate.

It will therefore be seen that the foregoing represents a highly advantageous approach to production of bioactive composites and prostheses having unique and easily varied mechanical properties. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A bioactive composite material comprising a solid-phase homo- or copolyolefin binder with a weight-average molecular weight greater than about 100,000 and less than about 1,000,000 having dispersed therein about 5% to about 50% by volume of particulate bioactive glass material comprised of about 42% to about 52% silicon dioxide, the remainder comprised of oxides of sodium, calcium, and phosphorous and having an average particle size ranging from about 0.5 μm to about 500 μm sufficient to achieve in vivo attachment by in vivo formation of hydroxyapatite from said bioactive glass material, the composite material exhibiting a Young's modulus comparable to a soft tissue measured at human physiological temperature and pressure.

2. The material of claim 1 wherein the soft tissue is selected from the group consisting of cartilage, tendons, ligaments, skin, tympanic membrane, gingiva, subcutaneous tissue and collagen-based connective tissue.

3. The material of claim 1 wherein wherein the material is further capable of bonding to cancellous or trabecular bone.

4. The material of claim 1 wherein the polyolefin comprises polyethylene, polypropylene, polybutylene, or a copolymer of ethylene and at least one of propylene, butylene and hexene.

5. The material of claim 4 wherein the polyolefin comprises linear polyethylene.

6. The material of claim 1 wherein the Young's modulus lies in the range 0.5–4.0 GPa.

7. The material of claim 1 wherein the particulate bioactive glass material ranges in size from 1.5–150 μm.

8. The material of claim 1 wherein the material also exhibits a tensile strength comparable to that of a soft tissue.

9. The material of claim 1 wherein the material also exhibits a fracture strain comparable to that of a soft tissue.

10. A bioactive composite material comprising a mono- or copolyolefin binder with a weight average molecular weight greater than about 100,000 and less than about 1,000,000 having dispersed therein about 5% to about 50% by volume of at least one particulate bioactive glass comprised of about 42% to about 52% silicon dioxide, the remainder comprised of oxides of sodium, calcium, and phosphorous and having an average particle size ranging from about 0.5 μm to about 500 μm sufficient to achieve in vivo attachment by in vivo formation of hydroxyapatite from said particulate bioactive glass when said composite is exposed to in vivo ambient body fluids in vivo.

* * * * *